United States Patent
Baliga et al.

(10) Patent No.: US 7,687,776 B2
(45) Date of Patent: Mar. 30, 2010

(54) GAS AND/OR FLAME IMAGING SYSTEM WITH EXPLOSION PROOF HOUSING

(75) Inventors: Shankar B. Baliga, Irvine, CA (US); John H. Park, Irvine, CA (US); John G. Romero, Rancho Santa Margarita, CA (US)

(73) Assignee: General Monitors, Inc., Lake Forest, CA (US)

( * ) Notice: Subject to any disclaimer, the term of this patent is extended or adjusted under 35 U.S.C. 154(b) by 9 days.

(21) Appl. No.: 11/971,413

(22) Filed: Jan. 9, 2008

(65) Prior Publication Data

US 2008/0251724 A1    Oct. 16, 2008

Related U.S. Application Data

(60) Provisional application No. 60/911,263, filed on Apr. 11, 2007.

(51) Int. Cl.
*G01N 21/00* (2006.01)
*G01J 5/00* (2006.01)

(52) U.S. Cl. .................. 250/338.5; 250/338.1

(58) Field of Classification Search ............. 250/338.5, 250/338.3, 338.2, 339.02, 339.03, 338.1; 356/437
See application file for complete search history.

(56) References Cited

U.S. PATENT DOCUMENTS

| | | | | |
|---|---|---|---|---|
| 4,142,417 A | * | 3/1979 | Cashdollar et al. | 374/110 |
| 4,529,881 A | * | 7/1985 | Ceurvels et al. | 250/353 |
| 4,560,875 A | * | 12/1985 | Crowder | 250/343 |
| 5,197,295 A | | 3/1993 | Pundak | |
| 5,430,293 A | | 7/1995 | Sato et al. | |
| 5,466,926 A | | 11/1995 | Sasano et al. | |
| 5,479,258 A | | 12/1995 | Hinnrichs et al. | |
| 5,867,264 A | | 2/1999 | Hinnrichs | |
| 6,271,900 B1 | | 8/2001 | Li | |
| 6,317,205 B1 | * | 11/2001 | Merklein | 356/239.2 |
| 6,680,778 B2 | | 1/2004 | Hinnrichs et al. | |
| 6,777,684 B1 | * | 8/2004 | Volkov et al. | 250/341.1 |
| 2006/0091310 A1 | | 5/2006 | Furry | |
| 2007/0114362 A1 | * | 5/2007 | Feng et al. | 250/208.1 |
| 2007/0120058 A1 | * | 5/2007 | Blackwell et al. | 250/338.1 |

* cited by examiner

*Primary Examiner*—David P Porta
*Assistant Examiner*—Faye Boosalis
(74) *Attorney, Agent, or Firm*—Larry K. Roberts

(57) ABSTRACT

A gas imaging system for remotely detecting gas emissions by passive images of infrared radiation includes an optical system having a field of view. The optical system has a lens, an optical filter system for filtering light passed through the lens, and a photosensitive array located at the focal plane of the optical system to produce multi-spectral infrared image data of a scene under observation. A multi-spectral image processing system is configured for processing the image data produced by the photosensitive array to detect hazardous gas emissions and to discriminate against infrared radiation emitted by false alarm sources. Some embodiments may be configured for flame detection. Other embodiments may be configured for gas and flame detection.

45 Claims, 4 Drawing Sheets

GAS AND/OR FLAME IMAGING SYSTEM WITH EXPLOSION PROOF HOUSING

This application claims the benefit of U.S. Provisional Application No. 60/911,263, filed Apr. 11, 2007, the entire contents of which are hereby incorporated by reference.

BACKGROUND

Hazardous gases and chemicals may undergo continuous monitoring during storage and operations such as transfer and processing to ensure that flammable or toxic levels of gases and vapors are not allowed to escape into the atmosphere. Traditional fixed gas detection systems are either of the point or open path types. In the former, the gas must come into physical contact with the point detector; the point detector is usually catalytic or optical for combustible gas detection, and either electro-chemical or solid state (metal oxide) for toxic gases such as hydrogen sulfide. With open path systems, a beam of infrared light from a lamp or laser traverses a predetermined path. The gas to be detected must cross this path.

BRIEF DESCRIPTION OF THE DRAWINGS

Features and advantages of the disclosure will readily be appreciated by persons skilled in the art from the following detailed description when read in conjunction with the drawings wherein.

DETAILED DESCRIPTION

Figure 1:
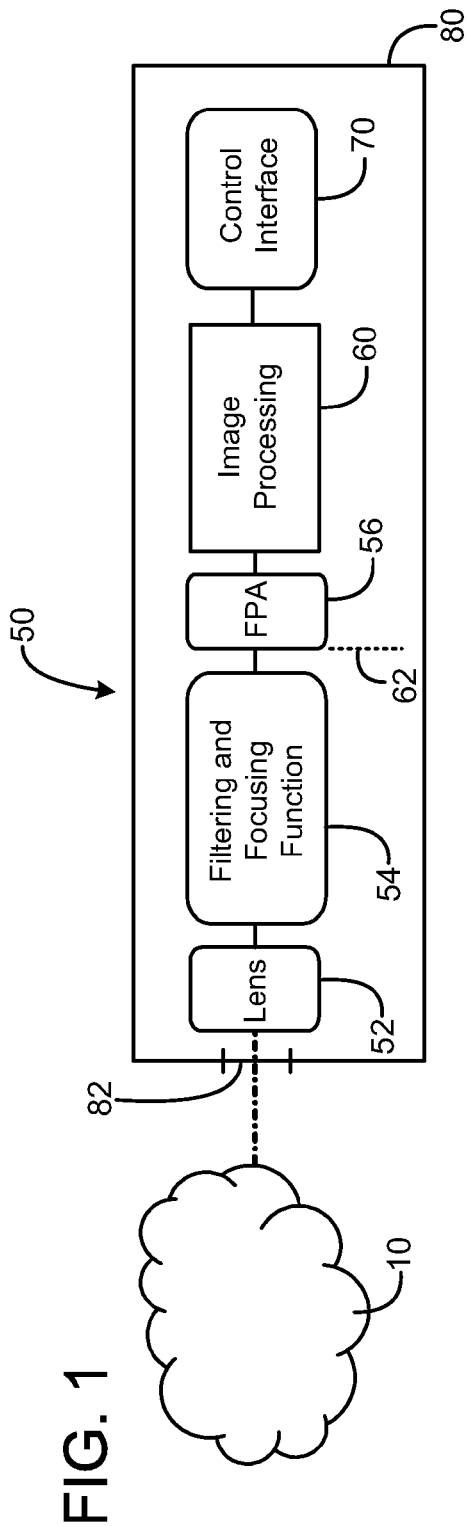
FIG. 1 is a schematic diagram of an exemplary embodiment of a detection system.

In the following detailed description and in the several figures of the drawing, the figures are not to scale, and relative feature sizes may be exaggerated for illustrative purposes. Like reference numbers may be used to refer to like or similar elements.

Exemplary embodiments of an apparatus and method for the detection of gas leak and/or flame emissions using the passive detection of infrared radiation are described.

FIG. 1 schematically illustrates an embodiment of a detection system 50 for detecting gas or flame represented generically as cloud 10. The system 50 includes an optical system with a field of view, and an image capturing device located in a fixed position at the focal plane of the optical system. In an exemplary embodiment, successive image frames gathered by the image capturing device representing captured scenes within the field of view of the system may be processed by image processing 60, to determine whether a particular gas is within the field of view of the system. The system 50 may also detect flames within the field of view. The gases or flames that can be detected by system 50 depend on the choice of the infrared pass band used, and the optical filtering function 54. An exemplary application for the system 50 is to provide a gas leak and/or flame detection apparatus that operates continuously in a fixed installation in a hazardous environment. The system may be transportable or portable.

In an exemplary embodiment, the system 50 includes an optical system with a lens 52, a filtering function 54 which may include some focusing functionality, depending on the implementation, and a photosensitive array 56 located at the focal plane of the optical system. The array 56 in an exemplary embodiment may be an uncooled two dimensional array of photosensitive elements, producing a frame of image data which can be read out from the array and processed by image processing 60. In this exemplary embodiment, the array 56 may be an uncooled, microbolometer array, fabricated using materials such as the oxides of vanadium, or amorphous silicon, at the focal plane of the optical system to form an infrared image of the scene under observation. Alternately, an uncooled ferroelectric or pyroelectric array can be used at the focal plane.

The focal plane array has a measure of sensitivity known as Noise Equivalent Temperature Difference (NETD); in an exemplary embodiment, a NETD value of less than 100 milliKelvins is desired and achievable using f/1 optics. Lower values of NETD can be obtained using cooled photodetector focal plane arrays such as mercury cadmium telluride arrays. The term "f/1" refers to the light gathering capability or relative aperture of the optics; the "1" implies a value of unity for the ratio of focal length to lens diameter. Smaller f number optics have better light gathering capability, since the signal to noise of an optical system can be shown to be inversely proportional to the square of the f/#. System performance using f/1 optics is a good benchmark.

Still referring to FIG. 1, the optical system includes a lens 52 designed for optimum infrared transmission in the mid infrared region of 2 to 5 microns. The lens 52 may be fabricated using conventional infrared transmissive materials such as quartz, silicon or germanium with additional anti-reflection coatings. Alternately, a lens made of infrared transmissive plastic, usually a Fresnel lens, can be employed. A wider infrared bandwidth such as 2 to 14 microns can also be utilized to cover both the mid and long wave infrared regions. A window 82 made of a mechanically strong, yet infrared transmissive material, such as 5 millimeter thick annealed sapphire, is mounted on the external housing 80 of the apparatus. A mechanically strong, optical window may provide for the explosion proof rating to operate the apparatus in a hazardous environment. It is also acceptable to use a mechanically strong lens as the outermost optical element to provide for an explosion proof or flame proof rating, if such a rating is desired for locating the system in a hazardous environment, e.g., outside a chemical plant or refinery.

An accepted method of protection for industrial sensors such as fire and gas detectors in North America is the explosion proof method, known as XP, which ensures that any explosive condition is contained within the sensor enclosure, and does not ignite the surrounding environment. In Europe, the term "flame proof," known as Ex d, is used for an equivalent method and level of protection; in this description, the terms "explosion proof" and "flame proof" are used synonymously to avoid global variations in terminology. There are established standards for explosion proof or flame proof systems, and systems can be certified to meet these standards. Some of the standards that are widely accepted by the industry and government regulatory bodies for explosion-proof or flame-proof designs are CSA C22.2 No. 30-M1986 from the Canadian Standards Association, FM 3600 and 3615 from Factory Mutual, and IEC 60079-0 and 60079-1 from the International Electrotechnical Commission.

In addition to mechanically strong optical elements mounted on the external housing 80, the external housing 80 itself is designed and fabricated to be mechanically strong to provide for the explosion proof rating.

If for a given application, the apparatus is not to be operated in a hazardous environment, the stringent requirements for hazardous location can be relaxed for a general purpose enclosure. Such can be the case if the optical system of the imaging system has a long enough range (hundreds of meters) that it can be mounted outside the hazardous environment, e.g., outside the chemical plant or refinery.

Figure 5:
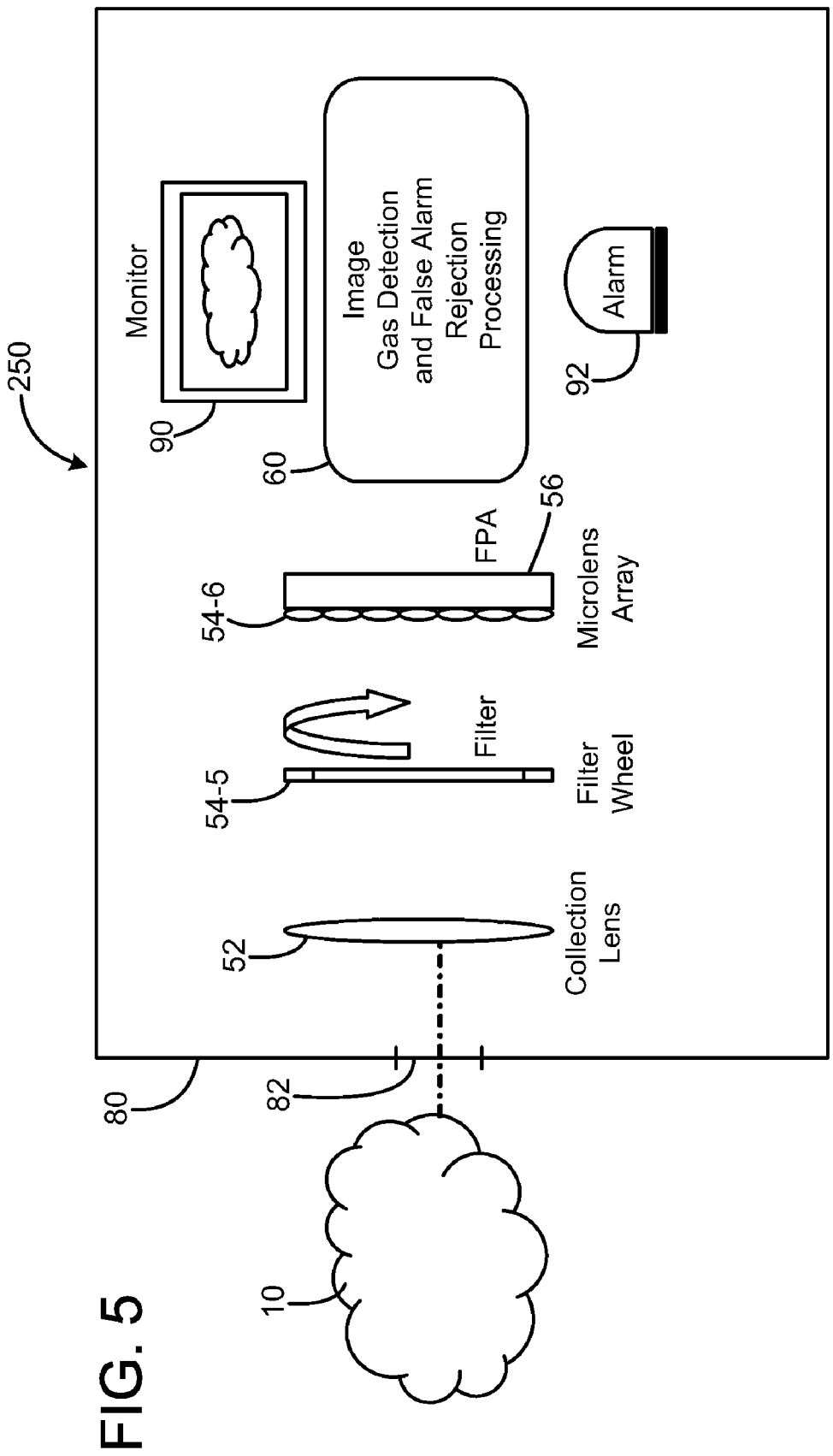
FIG. 5 is a schematic diagram of an exemplary embodiment of another detection system including a filter wheel and a microlens array.

Control interface 70 in an exemplary embodiment provides the interface of the system with the outside world. This could be via analog or digital communication, a graphic interface for control or monitoring by an operator, or a monitor 90 for viewing as shown in FIG. 5. In an exemplary embodiment, the system 50 may decide on the detection, quantification, speciation and localization using on-board image processing 60 without outside world intervention. The control interface 70 may provide a means to set the parameters of the system and to provide the processed information to the outside world.

In order to use the imaging focal plane array (FPA) 56 as a gas or flame detector, it may not be sufficient to use a broadband detector array along with the lens element 52. Some means to provide wavelengths suitable for measuring infrared gas absorption or flame emissions may be employed to allow the gas cloud or flame to be detected in the presence of infrared radiation from the thermal background. This function is provided in the exemplary embodiment of FIG. 1 by the filtering function 54.

Figure 2:
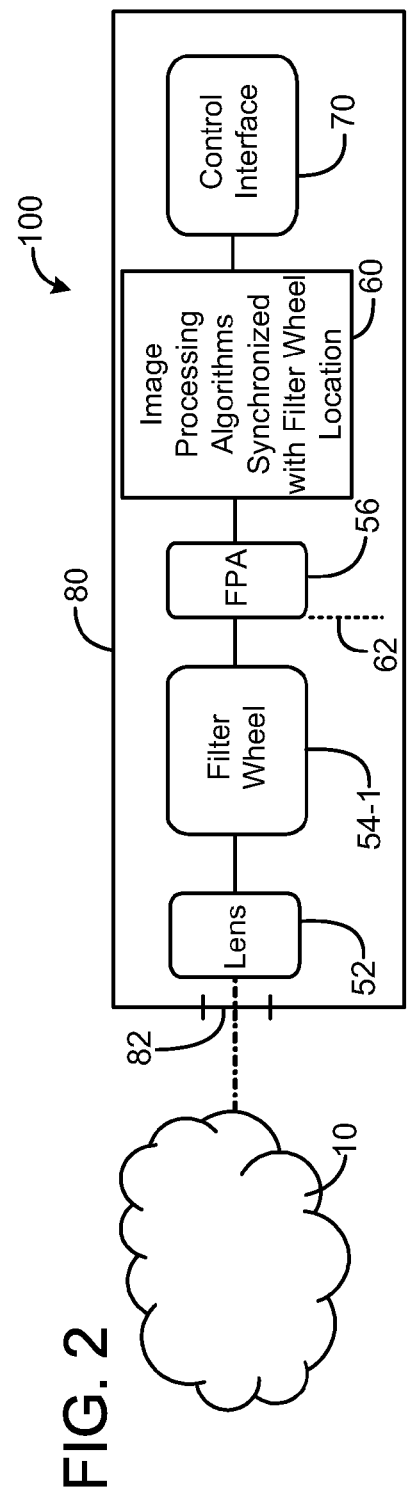
FIG. 2 is a schematic diagram of another exemplary embodiment of a detection system, employing a filter wheel housing multiple filters that are moved in a sequence across an imaging array.
Figure 6:
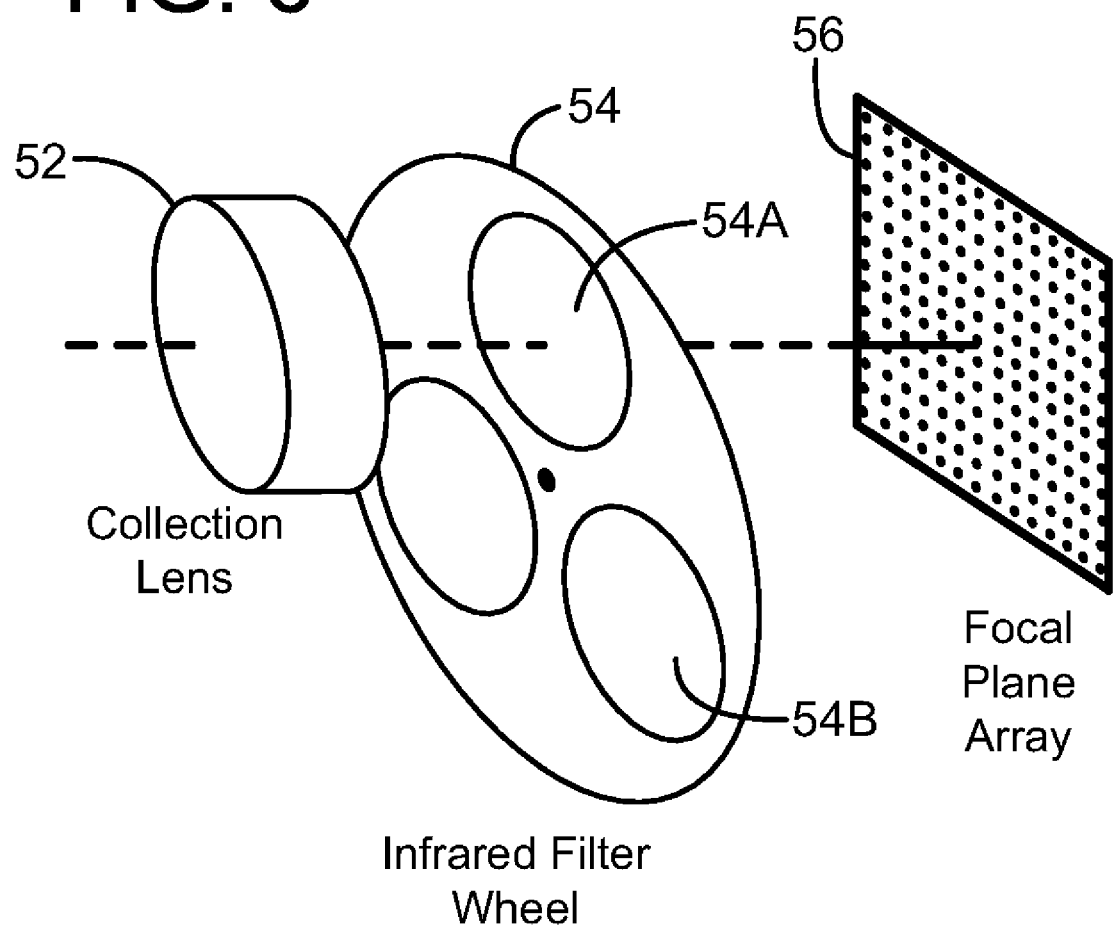
FIG. 6 is an isometric view illustrating an exemplary optical system for a detection system.

The exemplary detection system 50 of FIG. 1 employs image processing algorithms 60 to distinguish gas clouds or flame sources from other radiation sources via analysis of the spectral content, size, shape and evolution of the source. Exemplary image processing techniques include edge detection, frame subtraction, deconvolution, filtering and smoothing, and are described in references such as "Algorithms for Image Processing and Computer Vision" by J. R. Parker, John Wiley & Sons, 1997 (ISBN 0-471-14056-2) and "The Image Processing Handbook" by John C. Russ, CRC Press, 2006 (ISBN 0849372542). The motion of the false sources of radiation may also be accounted for, i.e. discriminated against, by such techniques. In an exemplary embodiment, this analysis is multi-spectral, i.e., it is performed over one or more sets of active and reference wavelengths. One exemplary means to provide a successive change of wavelengths or wavelength hopping is via the use of a filter wheel. FIG. 2 shows an exemplary embodiment of a detection system 100, in which a filter wheel 54-1 houses multiple filters that are moved in a sequence across the imaging array, typically by rotation about a center axis by a motor. The location of the filter wheel is synchronized with the image processing algorithms 60 in real-time. A frame of image data is obtained each time a filter element crosses the focal plane array 62. FIG. 6 illustrates an optical path in which a filter wheel houses multiple optical filters, which are rotated in a sequence to position a given one of the optical filters on the optical path so that energy illuminating the focal plane array has been filtered through the given one of the optical filters on the wheel.

The means to provide the absorption or emission wavelength selection, in this exemplary embodiment, is via the use of a narrowband infrared filter known as the active filter. The term "active" refers to the fact that the infrared radiation transmitted in this filter pass band is affected by the presence of the gas to be detected, due to molecular absorption. In the case of flame detection, the active filter is positioned at an infrared wavelength where flame emissions radiate energy strongly, e.g., 4.30 microns for hydrocarbon flame emissions. An example of an active filter for hydrocarbon gas detection is one centered at 3.335 microns. Additionally, to uniquely discriminate gas or flame radiation at the active wavelength from other sources of radiation emitting or absorbing at the same wavelength, a second filter known as the reference filter is employed in an exemplary embodiment. The term "reference" in this context refers to the fact that the infrared radiation transmitted in this filter pass band is not affected by the presence of the gas to be detected. In addition, the reference filter is positioned at an infrared wavelength where infrared radiation is not attenuated by the atmospheric gases such as carbon dioxide and water vapor. This is because most natural or manmade sources of radiation such as sunlight, welding and even human beings radiate sufficient infrared at such mid infrared wavelengths.

FIG. 6 illustrates an exemplary optical path in which lens 52 focuses radiation from the scene within the field of view onto a focal plane array 56 through filter wheel 54. The filter wheel is adapted to mount a plurality of optical filters, including active filter 54-A and reference filter 54-B. Preferably the filters are sized to substantially fill the focal plane array with incident filtered radiation. A combination of multiple active and reference filters can be used as described in the examples below.

Multi-spectral analysis with one or more of the goals of detection, quantification, speciation and localization may be performed through utilization of several filters in the filter wheel 54-1 (FIG. 2). Post-image processing and multi-spectral analysis may be performed by image processing 60. Additionally, the system may be capable of discriminating gas leak and flame emission signals from spurious sources of infrared radiation, with the choice of suitable reference wavelengths. To illustrate this further, typical filter combinations are described below:

a) For hydrocarbon gas detection the active filter is centered at 3.335 micron with a full width at half maximum (FWHM) bandwidth of 70 nanometers. Reference filters used could be at 2.2 microns, 3.16 microns and 4.90 microns with comparable bandwidths.

b) For gas detection with the additional ability to discriminate emissions from steam and water vapor, a filter at 2.95 microns sensitive to water vapor emissions can be added as an active filter.

c) For imaging of hydrocarbon flame emissions, the active filters are centered at 4.30 microns and 4.45 microns with a bandwidth of 250 nanometers. The reference filters are those from a) above.

d) For imaging of flames generating hot water vapor such as hydrogen, methane and other alkanes, the active filter at 2.95 microns can be added to the active filters set in c) or used as a substitute.

e) For multi-spectral analysis of both gas clouds and flames, suitable combinations of the above active and reference filters can be used. The reference filters described above are common to the different detection schemes, as their purpose is to provide multi-spectral information about background radiation and spurious sources of infrared radiation.

It should be understood that other suitable wavelengths and wavelength combinations can be used by those having ordinary skill in the art without departing from the spirit and scope of the invention. Some embodiments may be configured for gas detection. Other embodiments may be configured for flame detection. Still other embodiments may be configured for gas and flame detection.

In an exemplary embodiment utilizing a filter wheel (e.g. filter wheel 54-1 of FIG. 2), images of the scene within the field of view of the system are captured by the focal plane array 56 each time a filter crosses the array. Since the filters are at different reference and active wavelengths, the images created are multi-spectral and provide information about the background radiation as well as gas absorption and flame emissions. Discrimination against false alarms is provided by comparing the image generated at the reference wavelengths against those generated at the active wavelengths. The use of one or more reference filters ensures that radiation emitted or absorbed by spurious objects is not confused with that from flame emissions or gas clouds.

Table 1 summarizes the characteristic infrared absorption bands for typical hydrocarbon groups or families in the mid-infrared region. The alkane family includes gases such as methane, ethane, propane and butane, which comprise the constituents of natural gas. The aromatic family includes important chemicals such as benzene, xylene and toluene, while ethylene and propylene are part of the important family known as alkenes. The use of multiple filters at different gas absorption wavelengths provides the ability to speciate between the different hydrocarbon as well as non-hydrocarbon families using multi-spectral image processing techniques.

TABLE 1

Characteristic Infrared Bands

| Organic Group | Bond | Wavelength (microns) | Approximate Energy (Wavenumbers, cm$^{-1}$) |
|---|---|---|---|
| Hydroxyl | O—H | 2.74-2.77 | 3610-3640 |
| Amines | N—H | 2.85-3.03 | 3300-3500 |
| Aromatic Rings | C—H | 3.22-3.33 | 3000-3100 |
| Alkenes | C═C | 3.24-3.31 | 3020-3080 |
| Alkanes | C—C | 3.37-3.51 | 2850-2960 |

Figure 3:
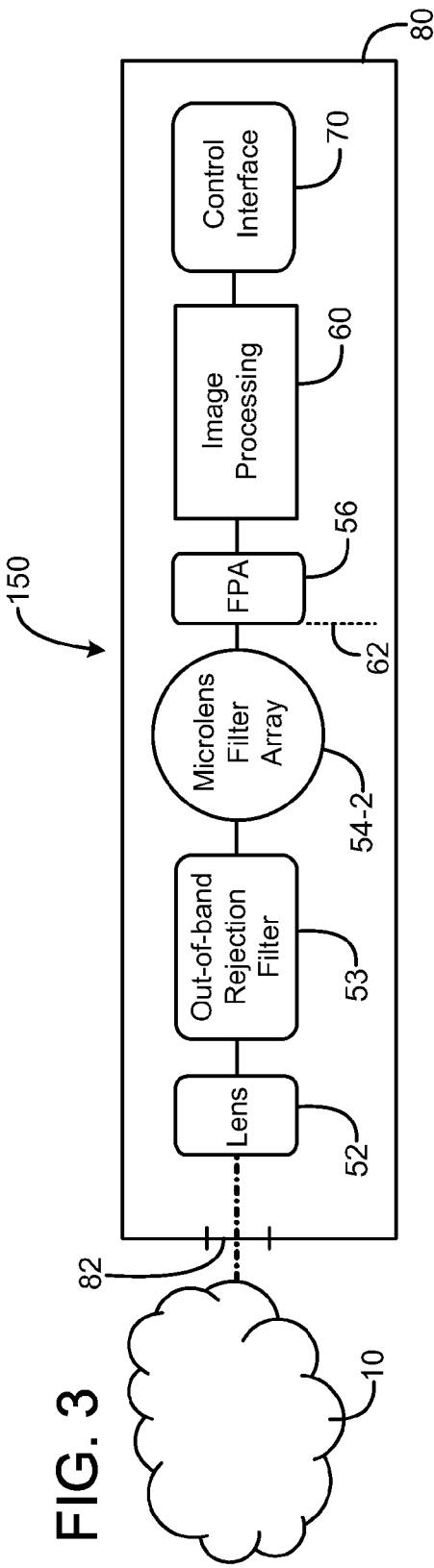
FIG. 3 is a schematic diagram of another exemplary embodiment of a detection system, employing a microlens filter array.

A second exemplary means to provide multi-spectral analysis of the received radiation is via the use of a microlens array. FIG. 3 illustrates a detection system 150, in which a two dimensional array of microlenses 54-2 is mounted over the imaging detector array 56. An ideal detector array is designed with no dead space between the individual detectors, but the demands of fabrication and circuit design may not permit the ideal detector array. The microlens array is able to reclaim this dead space by locating the array of microlenses with the same density as the individual photosensitive detectors of the array 56 one focal length from the plane of the array. Light destined for an inactive region around a detector element is collected by the microlens and directed onto the sensitive area of the detector. The microlens array may be fabricated using an infrared transmissive material such as sapphire, silicon or plastic.

Microlens arrays are known to suffer from chromatic aberration. This results in a large spread of the focal length with wavelength. Though this can be disadvantageous in most applications, in this exemplary embodiment, the microlenses are designed and fabricated so that different parts of the microlens array focus different infrared wavelengths on the detector array, using diffractive optical techniques. The microlens array may, therefore, be fabricated as a means to provide the multi-spectral information without the need for a filter wheel. Examples of how this may be achieved are described in U.S. Pat. No. 6,271,900 and U.S. Pat. No. 5,466,926. Since the diffractive optics techniques used to design microlens arrays can result in different orders or harmonics, the unwanted wavelengths are filtered out by an out of band rejection filter 53 (FIG. 3). The lens 52 in this scheme provides a collimated beam, which is focused by the microlenses onto individual pixels. Different pixels therefore receive energy at different infrared wavelengths, but from the entire scene under observation, or a group of pixels could receive energy at a particular infrared wavelength. The wavelength discrimination provided by the individual filters in the filter wheel is in this embodiment, provided by the microlenses or groups of microlenses. The microlens focal wavelength, diffractive order and rejection filter are designed so that the combination wavelengths described above in the filter wheel approach are achievable using the microlens array scheme. This second approach has the advantage of not requiring moving parts, as in the filter wheel embodiment. A frame of image data is acquired for image processing based on the thermal response time of the detector elements of the focal plane array. Post-image processing and multi-spectral analysis is performed to obtain the infrared image, which provides information on the location, size, gas species, concentration and motion of the gas leak or flame emission.

Figure 4:
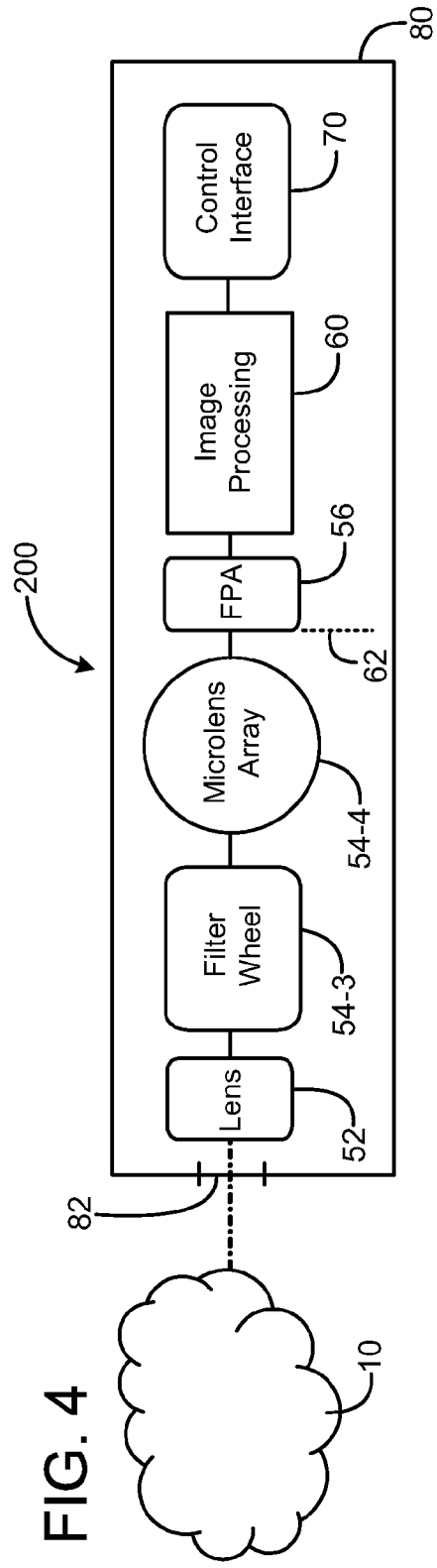
FIG. 4 is a schematic diagram of an exemplary embodiment of a detection system including a filter wheel and a separate microlens array.

In another approach, shown in FIG. 4, a detection system 200 is illustrated, in which a filtering and focusing function is provided by filter wheel 54-3 and a separate microlens array 54-4, with the microlens array providing light collection without a specific filter function. The microlens array in this approach focuses light over a wide bandwidth, while the moving filter wheel provides the wavelength modulation.

FIG. 5 is a schematic block diagram of a detection system 250, which includes a collection lens 52, a filter wheel 54-5, and a microlens array 54-6. In this embodiment, the microlens array 54-6 is fabricated on a surface of the focal plane array 56, i.e., not spaced one focal distance from the array 56. The image processing function 60 includes processing algorithms for image processing to provide detection of a gas such as propane in cloud 10, with appropriate false alarm rejection achieved through use of reference filters, as described above. If a gas is detected, an alarm 92 may be tripped. This may be a visual alarm, an audio alarm such as a siren, or an alarm signal sent back to a central station. The system 250 may also include a monitor 90 for displaying a visual representation of the detected image on its screen. This may allow a human observer to view the field of view, and observe a representation of the cloud 10. In one exemplary embodiment, the human observer is not required for operation of the instrument; it is optional for an observer to be present for human visual verification of the infrared image.

Although the foregoing has been a description and illustration of specific embodiments of the subject matter, various modifications and changes thereto can be made by persons skilled in the art without departing from the scope and spirit of the invention.

What is claimed is:

1. A gas imaging system for remotely detecting gas emissions by passive images of infrared radiation, comprising:
   an explosion proof housing structure configured to contain explosive conditions within the housing structure so as to not ignite a surrounding environment in which the gas imaging system is installed, the housing structure including an optical window fabricated of a mechanically strong, infrared transmissive material mounted on the housing structure to pass infrared radiation into the housing structure;

an optical system having a field of view and including a lens, an optical filter system for filtering light passed through the lens, and a photosensitive array located in a fixed position at the focal plane of the optical system to produce multi-spectral infrared image data of a scene under observation;

a multi-spectral image processing system configured for processing the image data produced by the photosensitive array to detect hazardous gas emissions and to discriminate against infrared radiation emitted by false alarm sources; and wherein the optical system and image processing system are disposed within the explosion proof housing structure.

2. The system of claim 1, wherein the photosensitive array is an uncooled, microbolometer array, at the focal plane of the optical system to form an infrared image.

3. The system of claim 2, wherein the microbolometer array is fabricated from an oxide of vanadium or from amorphous silicon.

4. The system of claim 1, wherein the photosensitive array is an uncooled ferroelectric or pyroelectric array.

5. The system of claim 1, wherein the photosensitive array is a cooled semiconductor array.

6. The system of claim 1, wherein the photosensitive array comprises a two dimensional array of photosensitive elements, producing successive frames of image data for processing by the image processing system.

7. The system of claim 1, wherein the focal plane array has a Noise Equivalent Temperature Difference (NETD) measure of sensitivity value of less than 100 milliKelvins.

8. The system of claim 1, wherein said image processing system is configured to process image data over one or more sets of active and reference wavelengths.

9. The system of claim 8, wherein said filter system includes a filter wheel housing multiple filter elements configured to be moved in a sequence across the imaging array by rotation about a center axis, and wherein the multiple filter elements include a first narrowband infrared filter having a passband for passing infrared energy in an active wavelength band of a gas whose presence is to be detected by the system, and a second filter having a passband for passing energy in a reference wavelength band of a false alarm or thermal background source.

10. The system of claim 9, wherein the image processing system includes image processing algorithms for processing the image data, and wherein the location of the filter wheel is synchronized with the image processing algorithms in real-time.

11. The system of claim 9, wherein a frame of image data is obtained each time a filter element crosses the photosensitive array.

12. The system of claim 1, wherein the lens is configured to produce a collimated beam of energy, and the system further includes:

a two dimensional array of microlenses disposed in an optical path between the lens and the photosensitive array, each microlens of the array configured to direct light destined for an inactive region around an element of the photosensitive array to a photosensitive area of the element of the photosensitive array.

13. The system of claim 12, wherein the microlens array is fabricated from an infrared transmissive material.

14. The system of claim 12, wherein the microlens array is configured so that different parts of the microlens array focus different infrared wavelengths on the detector array, using diffractive optical techniques.

15. The system of claim 12, wherein the microlens array is positioned one focal distance from the photosensitive array.

16. The system of claim 1, wherein the filtering system includes one or more active wavelength band filters and one or more reference wavelength band filters, the one or more active wavelength band filters for passing infrared energy in corresponding one or more wavelength bands of one or more gases whose presence is to be detected by the system, and the one or more reference wavelength band filters for passing energy in one or more wavelength bands of one or more false alarm or thermal background sources.

17. The system of claim 16, wherein the system is configured for hydrocarbon gas detection, and the one or more active wavelength band filters includes an active filter band centered at 3.335 micron, and the one or more reference wavelength band filters includes reference filters centered respectively at 2.2 microns, 3.16 microns and 4.90 microns.

18. The system of claim 16, wherein the system is configured for gas detection and to discriminate against emissions from steam and water vapor, and the one or more reference wavelength band filters includes a filter centered at 2.95 microns sensitive to water vapor emissions.

19. The system of claim 16, wherein the system is further configured for imaging of hydrocarbon flame emissions, and the one or more active wavelength band filters includes filters centered at 4.30 microns and 4.45 microns, and the one or more reference wavelength band filters includes reference filters centered respectively at 2.2 microns, 3.16 microns and 4.90 microns.

20. The system of claim 16, wherein the system is configured for imaging of flames generating hot water vapor from combustion of hydrogen, methane or other alkanes, and the one or more active wavelength band filters includes a filter centered at 2.95 microns.

21. The system of claim 1, wherein the window is an annealed sapphire window.

22. The system of claim 1, wherein the lens includes said window.

23. A stationary gas imaging system for remotely detecting gas emissions by passive images of infrared radiation, comprising:

an explosion proof housing structure including an optical window fabricated of a mechanically strong, infrared transmissive material to pass infrared radiation into the housing structure;

an optical system having a field of view and including a lens, an optical filter system for filtering light passed through the lens, and a photosensitive array located at the focal plane of the optical system to produce multi-spectral infrared image data of a scene under observation;

a multi-spectral image processing system configured for processing the image data produced by the photosensitive array to detect hazardous gas emissions and to discriminate against infrared radiation emitted by false alarm sources; and wherein the optical system and image processing system are disposed within the explosion proof housing structure; and wherein the system operates in a fixed installation in a hazardous environment.

24. The system of claim 23, wherein the photosensitive array is an uncooled array.

25. The system of claim 23, wherein the photosensitive array is a cooled array.

26. The system of claim 23, wherein the photosensitive array comprises a two dimensional array of photosensitive elements, producing successive frames of image data for processing by the image processing system.

27. The system of claim 23, wherein said image processing system is configured to process image data over one or more sets of active and reference wavelengths.

28. The system of claim 27, wherein said filter system includes a filter wheel housing multiple filter elements configured to be moved in a sequence across the imaging array by rotation about a center axis, and wherein the multiple filter elements include a first narrowband infrared filter having a passband for passing infrared energy in an active wavelength band of a gas whose presence is to be detected by the system, and a second filter having a passband for passing energy in a reference wavelength band of a false alarm or thermal background source.

29. The system of claim 28, wherein the image processing system includes image processing algorithms for processing the image data, and wherein the location of the filter wheel is synchronized with the image processing algorithms in real-time.

30. The system of claim 28, wherein a frame of image data is obtained each time a filter element crosses the photosensitive array.

31. The system of claim 23, including a two dimensional array of microlenses disposed in an optical path between the lens and the photosensitive array.

32. The system of claim 31, wherein each microlens of the array is configured to direct light destined for an inactive region around an element of the photosensitive array to a photosensitive area of the element of the photosensitive array.

33. The system of claim 31, wherein the microlens array is fabricated from an infrared transmissive material.

34. The system of claim 31, wherein the microlens array is configured so that different parts of the microlens array focus different infrared wavelengths on the detector array, using diffractive optical techniques.

35. The system of claim 31, wherein the microlens array is positioned one focal distance from the photosensitive array.

36. The system of claim 23, wherein the filtering system includes one or more active wavelength band filters and one or more reference wavelength band filters, the one or more active wavelength band filters for passing infrared energy in corresponding one or more wavelength bands of one or more gases whose presence is to be detected by the system, and the one or more reference wavelength band filters for passing energy in one or more wavelength bands of one or more false alarm or thermal background sources.

37. The system of claim 36, wherein the system is configured for hydrocarbon gas detection, and the one or more active wavelength band filters includes an active filter band centered at 3.335 micron, and the one or more reference wavelength band filters includes reference filters centered respectively at 2.2 microns, 3.16 microns and 4.90 microns.

38. The system of claim 36, wherein the system is configured for gas detection and to discriminate against emissions from steam and water vapor, and the one or more reference wavelength band filters includes a filter centered at 2.95 microns sensitive to water vapor emissions.

39. The system of claim 36, wherein the system is further configured for imaging of hydrocarbon flame emissions, and the one or more active wavelength band filters includes filters centered at 4.30 microns and 4.45 microns, and the one or more reference wavelength band filters includes reference filters centered respectively at 2.2 microns, 3.16 microns and 4.90 microns.

40. The system of claim 36, wherein the system is configured for imaging of flames generating hot water vapor from combustion of hydrogen, methane or other alkanes, and the one or more active wavelength band filters includes a filter centered at 2.95 microns.

41. The system of claim 23, wherein the lens includes said window.

42. A gas or flame imaging system for remotely detecting gas or flame emissions by passive images of infrared radiation, comprising:
   an explosion proof housing structure configured to contain explosive conditions within the housing structure so as to not ignite a surrounding environment in which the gas imaging system is installed, the housing structure including an optical window fabricated of a mechanically strong, infrared transmissive material mounted on the housing structure to pass infrared radiation into the housing structure;
   an optical system having a field of view and including a lens, an optical filter system for filtering light passed through the lens, and a photosensitive array located in a fixed position at the focal plane of the optical system to produce multi-spectral infrared image data of a scene under observation; and
   a multi-spectral image processing system configured for processing the image data produced by the photosensitive array to detect hazardous gas or flame emissions and to discriminate against infrared radiation emitted by false alarm sources; and
   wherein the optical system and image processing system are disposed within the explosion proof housing structure.

43. The system of claim 42, wherein the filter system includes one or more active wavelength band filters and one or more reference wavelength band filters, the one or more active wavelength band filters for passing infrared energy in corresponding one or more wavelength bands of one or more hazardous gases or flames whose presence is to be detected by the system, and the one or more reference wavelength band filters for passing energy in one or more wavelength bands of one or more false alarm or thermal background sources.

44. The system of claim 43, wherein the system is configured for imaging of hydrocarbon flame emissions, and the one or more active wavelength band filters includes filters centered at 4.30 microns and 4.45 microns, and the one or more reference wavelength band filters includes reference filters centered respectively at 2.2 microns, 3.16 microns and 4.90 microns.

45. The system of claim 43, wherein the system is configured for imaging of flames generating hot water vapor from combustion of hydrogen, methane or other alkanes, and the one or more active wavelength band filters includes a filter centered at 2.95 microns.

* * * * *